(12) United States Patent
Reinz

(10) Patent No.: US 8,392,902 B2
(45) Date of Patent: Mar. 5, 2013

(54) UPGRADING SOFTWARE APPLICATIONS OFFLINE USING A VIRTUAL MACHINE

(75) Inventor: Michael Reinz, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1136 days.

(21) Appl. No.: 11/877,983

(22) Filed: Oct. 24, 2007

(65) Prior Publication Data
US 2009/0113413 A1    Apr. 30, 2009

(51) Int. Cl.
*G06F 9/44* (2006.01)
*G06F 9/455* (2006.01)
*G06K 9/20* (2006.01)
*G01T 1/161* (2006.01)

(52) U.S. Cl. ........ 717/168; 717/170; 717/171; 717/173; 718/1; 382/128; 250/363.02

(58) Field of Classification Search .................. None
See application file for complete search history.

(56) References Cited

U.S. PATENT DOCUMENTS

| | | | | |
|---|---|---|---|---|
| 4,400,769 | A | | 8/1983 | Kaneda et al. |
| 5,845,128 | A | * | 12/1998 | Noble et al. .................. 717/170 |
| 6,075,938 | A | | 6/2000 | Bugnion et al. |
| 6,092,147 | A | | 7/2000 | Levy et al. |
| 6,330,709 | B1 | | 12/2001 | Johnson et al. |
| 7,076,778 | B2 | * | 7/2006 | Brodersen et al. ............ 717/170 |
| 7,770,164 | B2 | * | 8/2010 | Schuelein et al. ............ 717/168 |
| 7,784,044 | B2 | * | 8/2010 | Buban et al. .................. 717/168 |
| 8,051,414 | B2 | * | 11/2011 | Stender et al. ................ 717/168 |
| 2004/0103412 | A1 | * | 5/2004 | Rao et al. ....................... 717/171 |
| 2005/0063575 | A1 | * | 3/2005 | Ma et al. ........................ 382/128 |
| 2006/0080654 | A1 | * | 4/2006 | Shelton .......................... 717/173 |
| 2006/0271925 | A1 | * | 11/2006 | Schuelein et al. ............ 717/168 |
| 2007/0012880 | A1 | * | 1/2007 | Haider et al. ............. 250/363.02 |
| 2007/0277167 | A1 | * | 11/2007 | Smith et al. .................... 717/168 |
| 2008/0209409 | A1 | * | 8/2008 | Van Riel et al. ............... 717/168 |
| 2008/0271019 | A1 | * | 10/2008 | Stratton et al. ..................... 718/1 |
| 2008/0301676 | A1 | * | 12/2008 | Alpern et al. ..................... 718/1 |
| 2009/0031302 | A1 | * | 1/2009 | Beigi et al. ........................ 718/1 |

OTHER PUBLICATIONS

Montgomery, J., A Model for Updating Real-Time Applications, Real-Time Systems vol. 27, Jul. 2004, pp. 169-189, [retrieved on Oct. 11, 2012], Retrieved from the Internet: <URL:http://www.springerlink.com/content/n024l2165q18k816/fulltext.pdf>.*

Kol, T. et al., A Next Generation Enterprise Medical Object Management System (MOMS) Architecture, Proceedings of SPIE vol. 5371, 2004, pp. 239-250, <URL:http://proceedings.spiedigitallibrary.org/ConferenceProceedings.aspx>.*

* cited by examiner

*Primary Examiner* — Thuy Dao
*Assistant Examiner* — Geoffrey St Leger
(74) *Attorney, Agent, or Firm* — Lempia Summerfield Katz LLC

(57) ABSTRACT

A system and method upgrade software applications offline using a virtual machine. Software applications used by actual customer machines may rely upon customer specific data and protocols. An upgraded version of a software application may become available. The upgrade may be loaded onto a virtual machine. Customer specific data or protocols associated with a previous version of the application may be copied to the virtual machine. The upgraded version may be modified on the virtual machine using the data associated with the previous version. The upgrade process using the virtual machine may detect and eliminate problems with the upgrade associated with the customer machine and/or settings. Once modified, the upgraded version may be transferred from the virtual machine to the customer machine. The upgrade process may be performed primarily on the virtual machine. Therefore, the downtime of the customer machine required to complete the upgrade process may be substantially reduced.

20 Claims, 5 Drawing Sheets

UPGRADING SOFTWARE APPLICATIONS OFFLINE USING A VIRTUAL MACHINE

FIELD

The present invention relates generally to software applications that assist a user. More particularly, the present invention relates to upgrading software applications installed on actual customer machines located at various customer facilities using virtual machines.

BACKGROUND

Interactive software applications are installed on customer computers, systems, and/or other machines and used by customer personnel at various customer locations. The interactive software applications may be directed toward a wide array of applications, including medical applications. As an example, the software applications may assist medical personnel located at hospitals and other medical facilities to diagnose and treat patients. The software applications may support medical imaging techniques and devices, and/or facilitate maintaining and updating medical files associated with individual patients. The software applications may be directed toward other types of applications as well, both medical and non-medical.

Periodically, software applications in use are revised and updated. However, the installation of the software upgrades may be cumbersome and time intensive. The installation process may require downtime, during which the customer machine is not available for use.

For instance, customer personnel may install the revised software. Alternatively, an experienced software technician may travel to each customer facility and install the software upgrades on the customer machines. At the customer facility, the technician may have to initially back-up all the user-specific data and customized application settings. After saving the customized application settings, the technician may install the new version of the software application. Subsequently, the technician may re-install the saved customized settings.

After the new version of the application is installed, so-called client or customer protocols, such as hardware and configuration specific protocols, may have to be converted to become compatible with the new version of software. As noted, during the entire software upgrade process, the customer's machine may be occupied and unavailable for use by the customer.

Additionally, some of the software upgrade related operations may be performed by a software technician using another actual machine that is similar to the customer machine, such as a machine that is located at a remote service center. However, performing software upgrade related operations or modifications on another actual machine may have associated high overhead costs, such as the maintenance and upkeep of a dedicated actual computer and/or medical system.

BRIEF SUMMARY

A system and method upgrade software applications offline using a virtual machine. Software applications used on actual customer machines may rely upon customer specific data and customer protocols. A revised or updated version of a software application ("upgrade") may be released. The upgrade may be loaded onto a local or remote virtual machine. The customer specific data and/or customer protocols that the previous version of the software application implemented on the actual customer machine may be copied to the virtual machine. The upgraded version of the software application may be modified or tailored on the virtual machine using the customer specific data and/or customer protocols from the actual customer machine. The modified upgraded version of the software application that is tailored based upon the customer related data may then be transferred from the virtual machine to the actual customer machine. The upgrade process may be performed entirely, primarily, or at least in part, on the virtual machine. The upgrade process using the virtual machine may detect and eliminate problems with the upgraded version as modified based upon customer data, settings, customizations, and/or machine specifications before transfer to the customer machine. As a result, the downtime of the customer machine required to complete the upgrade process may be minimized as most, if not all, of the upgrade process, including testing and troubleshooting, is completed by and/or using the virtual machine offline, which allows the customer machine to substantially or completely remain online and operational.

In one embodiment, a method upgrades software offline using a virtual machine. The method includes creating a virtual machine that mimics an operation of an actual customer machine, loading an upgraded version of a software application onto the virtual machine, and loading customer specific data related to a previous version of the software application onto the virtual machine, the previous version of the software application being installed on the actual customer machine. The method also includes modifying the upgraded version of the software application on the virtual machine using the customer specific data such that the upgraded version of the software application as modified is compatible with the actual customer machine without further modification and transferring the upgraded version of the software application as modified from the virtual machine to the actual customer machine for use on the actual customer machine.

In another embodiment, a method upgrades software offline via a virtual machine. The method includes loading an upgraded version of a software application onto a virtual machine that is configured to mimic an operation of a customer machine, transferring customer protocol data identifying customer protocols related to a previous version of the software application installed on the customer machine from the customer machine onto the virtual machine, and modifying the upgraded version of the software application to become compatible with the customer machine using the virtual machine and the customer protocol data. The method also includes transferring the modified upgraded version of the software application from the virtual machine to the customer machine such that the modified upgraded version of the software application can be run on the customer machine.

In another embodiment, a virtual machine upgrades software offline. The virtual machine includes a memory unit storing an upgraded version of a software application, and a processing unit configured to receive, from a customer machine, customer specific data related to the operation of a previous version of the software application on the customer machine. The virtual machine automatically modifies the upgraded version of the software application stored in the memory unit based upon the customer specific data received by the processing unit and creates an executable modified upgraded version of the software application that can be run by the customer machine without further modification.

In yet another embodiment, a computer-readable medium provides instructions executable on a computer. The instructions direct the operation of a virtual machine that mimics a customer machine in a virtual machine mode, receiving customer related data from the customer machine related to a previous version of a software application installed on the customer machine, and modifying an upgraded version of the software application based upon the customer related data. The instructions also direct testing the modified upgraded version of the software application via the virtual machine operating in the virtual machine mode to verify that the modified upgraded version is executable on the customer machine, and transferring the modified upgraded version of the software application to the customer machine for use.

Advantages will become more apparent to those skilled in the art from the following description of the preferred embodiments which have been shown and described by way of illustration. As will be realized, the system and method are capable of other and different embodiments, and their details are capable of modification in various respects. Accordingly, the drawings and description are to be regarded as illustrative in nature and not as restrictive.

DETAILED DESCRIPTION

Figure 1:
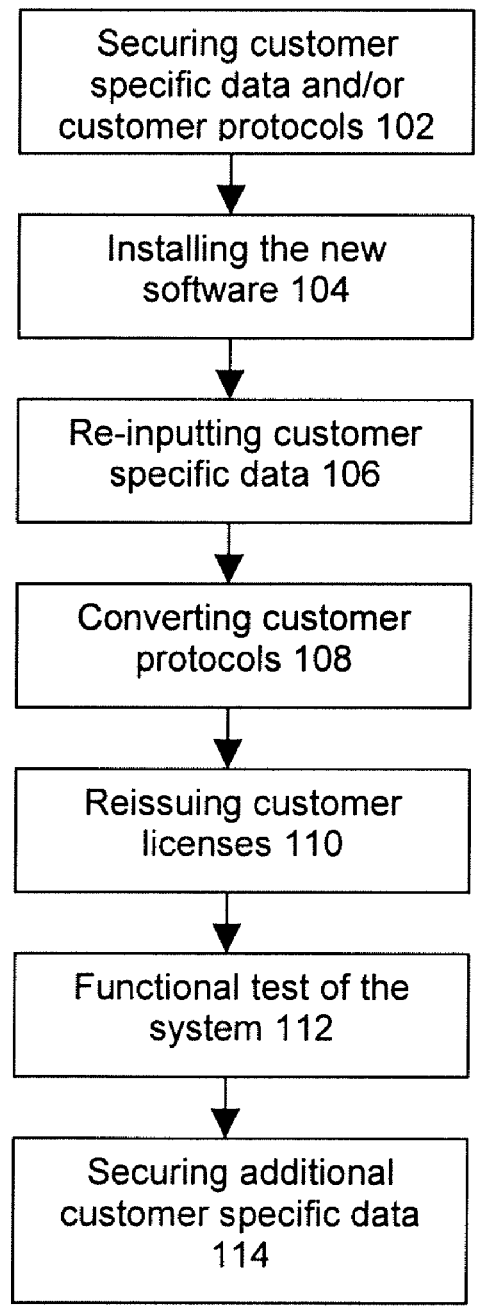
FIG. 1 illustrates a conventional method of upgrading a software application at a customer location.

A system and method upgrade software applications offline using a virtual machine. Interactive software applications used by customer personnel on actual customer machines at various customer facilities may rely upon customer related data, such as customer specific data and customer protocol data. A revised or updated version of an interactive software application ("upgraded version") may become available for use. The upgraded version may be loaded onto a system configured to perform as a virtual machine that simulates an actual customer machine. The virtual machine may be locally implemented, such as on a portable laptop, or remotely implemented at a remote customer service facility.

An upgrade process may be performed entirely, primarily, or at least in part, on the virtual machine. The customer specific data and/or customer protocols that the previous version of the software application implemented on an actual customer machine may be copied or otherwise transferred to the virtual machine. An upgraded version, or even the original version of a software application if copied to the virtual machine, may be modified on the virtual machine using the customer specific data, the customer protocols, and/or other customer related data received from the actual customer machine.

The upgraded version (such as either a revised version or a revised previous version transferred from the customer machine, for instance, an original or previous version may be modified by adding new routines or functionality) of the software application modified to account for the customer specific data and/or customer protocols may then be transferred from the virtual machine to the actual customer machine. The upgrade process using the virtual machine may detect and eliminate problems with the upgrade before the upgraded version is transferred to the actual customer machine. As a result, the downtime of the actual customer machine required to complete the upgrade process, i.e., the amount of time that the physical customer machine is taken offline, including testing and troubleshooting, may be minimized or even eliminated.

Maximizing the time that the customer machine is available for use may be especially important for complex medical software applications, such as Syngo™ imaging software, which currently may require up to two or three days to upgrade using conventional techniques. A disk image backup of the Syngo™ software may be generated or copied from an actual Syngo™ imaging system. The backup may then be moved to a virtual machine. Alternatively, a copy of the actual Syngo™ imaging system software may be transferred directly to the virtual machine, such as over a network, without the use of a portable storage medium. The upgrade process may then be performed using the virtual machine. As a result, any problems associated with the upgrade may be detected and eliminated by modifying the upgraded version of the imaging system software while on the virtual machine and before transfer to the actual customer machine. Other applications may be upgraded.

Once the modified upgraded version of the software application is transferred to the customer machine, an associated customer software license may be reissued. Optionally, after the installation of the modified revised version of the software application on the customer machine is completed, a functional test of the modified upgrade version may be performed using the actual customer machine. Alternatively, the upgraded version of the software application is modified to account for customer data, settings, customizations, and/or actual machine specifications and may be executable on the customer machine without further modification and/or testing. Testing of the modified upgrade may be performed solely or primarily on the virtual machine operating in a virtual mode of operation that mimics one or more operations or functions of the actual customer machine.

In general, the software applications may employ the capabilities of a computer directed toward a task that the customer wishes to be performed. The software applications may provide one or more particular functions, such as a word processor or a database function. In one embodiment, the software applications are directed to the field of medicine and assist medical personnel with the diagnosis of medical conditions and the treatment of patients. However, alternate software applications may be upgraded and modified via a virtual machine tailored to mimic the customer machine.

The customer specific data may include all of the individual customer data and settings used by the software application on the actual customer machine. The customer specific data may be needed to restore the complete software application. The customer specific data may enable the restoration of a customized user interface, i.e., the overall "look and feel" of the previous version of the software application as used on the customer machine. The customer specific data may relate to customer customizations, configurations, operating systems, interfaces, interconnectivity, other applications, and/or settings.

As an example, the customer specific data may be used to restore a graphic user interface of the software application, parameter settings, individual menu settings, the functionality of one or more particular macros, modules, or subroutines, or other portions of the software application. The customer specific data may be used to upgrade and/or restore user specific functions and their corresponding properties associated with the software application. The customer specific data may relate to additional, fewer, or alternate types of individual customer customized data, settings, and/or functionality.

The customer protocols may account for hardware and hardware configurations, as well as the software configurations. The customer protocols may include all settings and parameters related to the type of computers and/or machines that the software application operates on at the customer location. For example, the customer protocols may be manufacturer, supplier, or distributor specific and depend upon the manufacturer of the actual computer and/or machine. The customer protocols may depend upon the application to which the actual computer and/or machine is put. The customer protocols may account for specific modules, macros, and subroutines of the software application. Additional, fewer, or alternate customer protocols may be used.

The customer machines may be implemented at geographically dispersed customer facilities located some distance away from a remote customer service center. The customer service center may be a location from which software technicians and field engineers are located and/or modify upgraded versions of pre-existing software applications. Customer data related to a previous version of a software application, such as the customer specific data and/or customer protocols discussed herein, may be transferred from a customer machine to either a local or remote virtual machine. The local virtual machine may be a portable computer that a service technician brings to the customer location.

Alternatively, the virtual machine may be located at the remote customer service center. The transfer of the customer related data, such as customer specific data and/or customer protocols, to a remote virtual machine over a network may eliminate the need for the field engineers to travel to a customer location to retrieve the customer related data. The transfer of the customer related data to a remote virtual machine over a network also may eliminate the need for the field engineers to locate, identify, and save the customer specific data, customer protocol, and/or other customer related data in the field (i.e., at the customer's location). For instance, the customer related data may be located and identified for transfer to the virtual machine, either via a network or a portable medium, automatically by a software program written by a software expert. Such a program may operate in the background on the customer machine so as to not interfere with the availability of the customer machine for use by customer personnel.

Upgrading the customer's version of the software application using the customer's machine may substantially occupy the customer's machine, which interferes with and degrades the effective use of the machine by customer personnel. Hence, the elimination of upgrading the software directly on the customer's machine may reduce the amount of time that an actual machine is unavailable for use by customer personnel.

The upgraded version of the software application may be modified on a local or remote virtual machine using the customer related data, including the customer specific data and/or customer protocols, received from the customer's machine. The modification of the upgraded version of the software application using the virtual machine may eliminate the need for the field engineer, at the customer location and using the actual customer machine, to (1) install a clean upgraded version of the software application on the actual customer machine, (2) re-input all of the customer specific data after installation of the upgraded version of the software application, and (3) convert the customer protocols to become compatible with the upgraded version of the software application. The reduction in the amount of work that the field engineer, or even the customer, performs at the customer location occupying the customer's machine may reduce the amount of time that the customer's machine is unavailable for its intended use.

In one embodiment, the upgraded version of the software application may be installed or loaded on the virtual machine. The virtual machine may be configured to provide functionally comparable or equal to the actual customer machine or otherwise simulate the customer machine. The customer specific data and/or customer protocols received from the actual customer machine associated with a previous version of a software application may be installed, loaded, or saved on the virtual machine. After which, a customized and executable version of the upgraded version of the software application may be generated that accounts for the customer related data associated with the previous version of the application. The executable version may be uploaded to the customer's machine via remote network interconnection or portable storage medium to replace the previous version of the software application.

I. Conventional Online Upgrade Technique

FIG. 1 illustrates a conventional method of upgrading a software application at a customer location. Typically, software applications would be upgraded in the field. A software technician or field engineer would travel to a customer location where the software application is installed on one or more local computers and machines. At the customer location, the field engineer may back up all of the individual customer data and settings utilized by the software application. The back up data may be used to restore the complete software application.

As shown in FIG. 1, at the customer location, the software technician typically initially saves customer specific data and/or customer protocol data 102. The software technician installs a new or revised version of the software application 104 and re-inputs the customer specific data 106. The software technician also converts the customer protocols 108 to become compatible with the revised version of the software application.

In many cases, because of the detailed nature of software application licenses, a new customer software license is issued 110. The new software licenses are typically requested from a central licensing office. After which, a functional test of the actual system 112 may be performed. Additionally, customer specific data 114 may be obtained specific to the revised version of the software application. During the entire conventional upgrade process, the customer's actual machine may be occupied by a field engineer, which prevents or limits the effective use of the machine by customer personnel.

II. Exemplary Offline Upgrade Techniques

Performing some, most, or all of the steps involved with upgrading software applications on a virtual machine may reduce the amount of work performed by field engineers occupying the actual customer machine. By reducing the amount of work involved with upgrading software applications performed on the actual customer machines, the amount of time that customer personnel may effectively use the customer machine is increased.

Transferring the work performed by software technicians and engineers to a virtual machine may increase effectiveness and efficiency. Not only can customer personnel continue to use the actual customer machine without interference by field engineers, the field engineers may perform the upgrade process without interference by customer personnel or having only intermittent use of or access to the customer machine. Additionally, although field engineers may backup customer data related to the customer machine locally, after the upgraded version of the software application has been modified to account for the customer machine customized settings, specifications, and type, the modified upgraded version may be remotely transferred to and uploaded on the actual customer machine, which may reduce travel time to the customer location. Increasing the amount of work performed by the engineers on a virtual machine may reduce errors in the upgrade process as the internal upgrade process using the same virtual machine may be substantially replicable.

Figure 2:
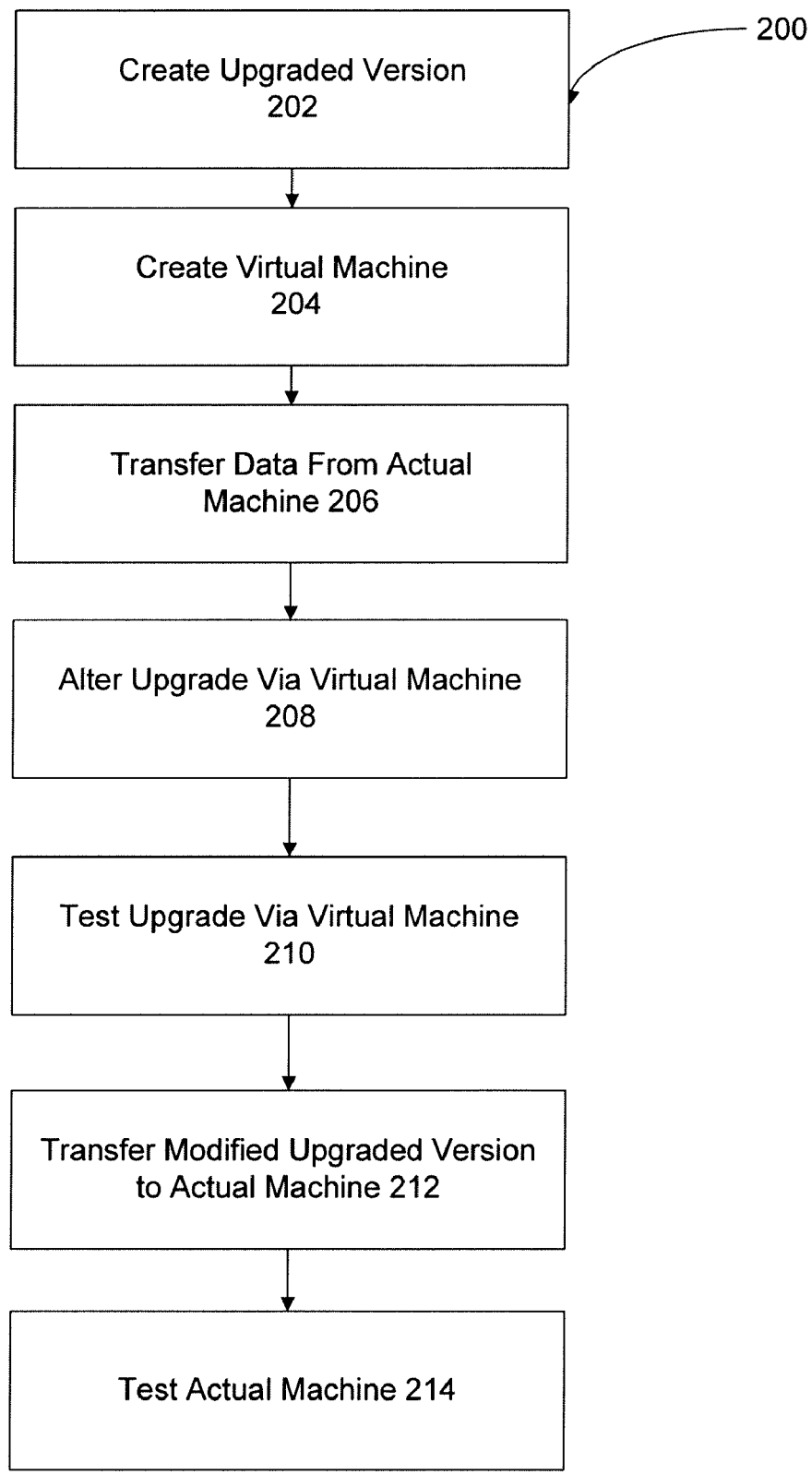
FIG. 2 is an exemplary technique for upgrading a software application offline via a virtual machine.

FIG. 2 is an exemplary method 200 for upgrading a software application offline via a virtual machine. The method 200 may include creating an upgraded version of a software application 202, creating a virtual machine 204, transferring data from an actual customer machine 206, altering the upgraded version of the software via the virtual machine 208, testing the modified upgraded version of the software via the virtual machine 210, transferring the modified upgraded version to the actual customer machine 212, and testing and using the upgraded version on the customer machine 214. The method may include additional, fewer, or alternate actions.

The method 200 may include creating an upgraded version of a software application 202. The upgraded version of the software application may be an updated or a revised version of an existing software application that is being used on an actual customer machine. Alternatively, the upgraded version may be an entirely new software application that is to be modified via a virtual machine using customer related data, such as customer specifications and preferences, and then installed on a customer machine. The upgraded version may add new functionality, routines, and software related operations to a previous version of the software. Other upgraded versions may be used.

The method 200 may include creating a virtual machine 202. For illustrative purposes, conventional virtual machines are disclosed by U.S. Pat. Nos. 4,400,769; 6,075,938; 6,092,147; and 6,330,709, which are incorporated herein by reference in their entireties. In one embodiment, the virtual machine may be supplemented by an available software tool known as VMware™. Other virtual machines and/or software tools may be used.

For instance, the virtual machines discussed herein may include substantially more functionality than that provided by conventional virtual machines and related software tools. In one embodiment, the virtual machine may simulate a wide range of operations/functionality associated with an actual medical imaging system, such as a Syngo™ imaging system.

The virtual machine may be programmed by a software expert to simulate or mimic one or more operations of a customer machine. As a result, the upgrade process may not require either occupying the customer machine or another comparable actual machine. Instead of incurring the costs of taking the customer machine offline to perform the upgrade process or maintain a dedicated machine for upgrade purposes, creating a re-usable virtual machine that simulates the actual hardware may be much more cost effective.

The virtual machine may be a laptop or other computer that simulates a number of different hardware configurations and/ or actual machines. The virtual machine may mimic various types of networks (including wired, wireless, intranet, local communication, and local area networks), network connections, baud rates, and other hardware or software features.

The virtual machine may simulate interconnectivity with an email system, the Internet, an intranet, an extranet, and account for various interfacing protocols. The virtual machine may simulate differing types and levels of security measures, such as different levels of user access, passwords, usernames, and logins. The virtual machine may model or mimic various file management, storage, creation, transfer, and restoration systems and applications.

The virtual machine may simulate various operating systems, kernals, and/or software levels between the operating system and applications. The virtual machine may mimic various output devices, such as printers or display screens. The virtual machine may simulate functionality related to voice recognition or providing audible, graphical, video, textual, or visual instructions.

The virtual machine may accept and model user settings and protocols for various hardware and software embodiments, and various software versions. The virtual machine may model various types of monitors and screens, such as split screens and/or interfaces that employ a number of input devices, including a keyboard, a mouse, a light pen, a touch pad, a touch screen, or other input means. The virtual machine may simulate various types of user interfaces or graphical user interfaces, such as text or windows based interfaces.

The virtual machine may model control of specific customer machines, such as customer machines related to the control and manipulation of imaging devices or control of devices used in electrophysiology labs, operating rooms, or emergency rooms. The virtual machine may be programmed to simulate functionality related to picture archiving and communications systems (PACS), data mining, medical imaging techniques, fusion of multi-dimensional anatomical data (such as ultrasound, computed tomography, x-ray, magnetic resonance, and other medical images), rotation of medical images, virtual flight through hollow organ images, and medical imaging device operation. The virtual machine may simulate patient data re-organization or image scrolling, such as leafing through multi-dimensional image data. Additional, fewer, or alternate operations and functionality may be provided by the virtual machine.

The method 200 may include transferring data from an actual customer machine 206 to the virtual machine. The data may be transferred from the actual machine to the virtual machine while the actual machine is simultaneously performing other operations, such as operations associated with its intended use (such as acquiring medical images if the customer machine is a medical imaging system). For instance, the actual machine may have a separate routine that runs in parallel with its main operations that controls data transfer. Alternatively, the virtual machine may control the data transfer over a network, or the data may be transferred via a portable storage medium.

In one embodiment, the customer related data may be located and identified for transfer to the virtual machine automatically by software functionality programmed by a software expert. Such software functionality may operate in the background on the customer machine so as to not interfere with the availability of the customer machine for use by customer personnel. The software may automatically identify customer specific data, customer protocols, and other customer related data, including customer customizations and preferences, and other data discussed herein, associated with the operation of the previous version and/or the upgraded version of the software application.

The customer related data transferred may include data associated with customer software and/or hardware, including data related to customer specifications, configurations, settings, customizations, and other customer and/or customer machine related data. The customer related data transferred may include customer specific data and customer protocol data as discussed herein. The data transferred may be loaded, installed, or otherwise saved on the virtual machine or an associated memory unit. Additional, fewer, and alternate types of data may be transferred.

The method 200 may include altering an upgraded version of software via the virtual machine 208. The virtual machine may modify the upgraded version using the customer related data received from the customer machine, including the customer specific data and the customer protocol data. The virtual machine may perform automatic modifications or assist a technician with implementing manual modifications. The automatic or manual modifications may be performed with the virtual machine operating in a virtual mode. In the virtual mode of operation, the virtual machine may simulate one or more operations of the actual machine.

The virtual machine may employ a number of tables and/or rule sets. The rules may correlate the customer related data, such as settings, specifications, customizations, and functionality with predetermined modifications to the upgraded version that must be accomplished to ensure compatibility with the customer machine. Other automatic modifications may be used.

The method 200 may include testing the modified upgraded version of software via the virtual machine 210. A number of tests may be automatically performed by the virtual machine. For instance, the virtual machine may check that the modified upgrade has been modified to properly account for the customer related data, such as the customer specific data and/or customer protocols. For instance, a number of variables or settings within the upgraded version may be checked to verify that they correspond with the customer settings, modifications, customizations, etc. identified by the customer related data.

Alternatively or additionally, a number of tests may be performed manually with the assistance of the virtual machine. The testing may be performed with the virtual machine operating in a virtual machine that mimics the customer machine. Testing the modified upgrade in a virtual mode may facilitate troubleshooting any problems associated with running the upgrade on the customer machine, as well as ensure the compatibility of the modified upgrade with the actual machine and that the functionality of the modified upgrade is reliable, all while the actual machine remains available for use.

The method 200 may include transferring the modified upgraded version to the actual customer machine 212. The modified upgrade may be transferred from the virtual machine to the actual machine while the actual machine is simultaneously performing other operations, such as operations associated with its intended use. For instance, the actual machine may have a separate routine that runs in parallel with its main operations that controls file transfer and upload. Alternatively, the virtual machine may direct the file transfer.

The modified upgraded version transferred to the customer machine may be an executable version that can be properly run or executed on the customer machine without further modification. For example, the virtual machine may have previously accounted for the type of customer machine and the preferred customer customizations and settings, and modified the upgrade accordingly.

The method 200 may include testing and using the modified upgraded version on the customer machine 214. Once on the actual customer machine, the modified upgrade may be tested once again. After which, the modified upgrade may be used on the customer machine to achieve its desired purpose.

Figure 3:
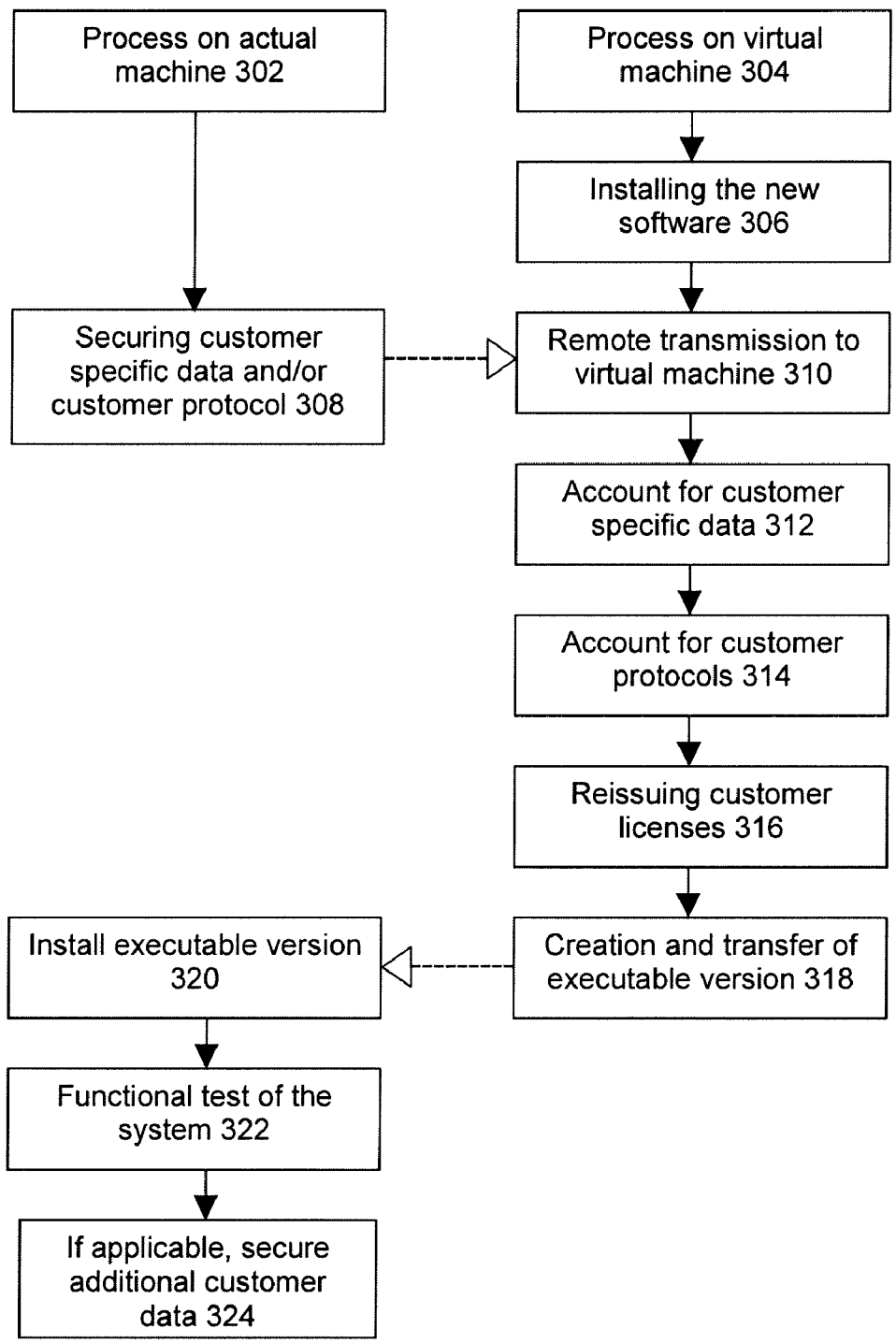
FIG. 3 is another exemplary technique for upgrading a software application offline via a virtual machine.

FIG. 3 is another exemplary technique for upgrading a software application offline via a virtual machine. The left hand side of FIG. 3 illustrates steps performed on or by accessing a customer machine 302 and the right hand side illustrates steps performed on a virtual machine 304.

An upgraded version of a software application being used by the customer machine may be loaded onto a virtual machine 306. The virtual machine may be operable to simulate the customer machine and/or customer machine functionality. As a result, the upgrade process may be implemented without occupying or requiring the use of an actual machine that is comparable or equal to the customer's machine. Other virtual machines may be used. The upgraded version of the software application may be a complete new version of the software application, a partial new version of the software application, an add-on or update of the previous version of the software application, or other software that provides new functionality for the software application.

The customer specific data and/or customer protocol data for a software application, as being used on the customer machine, may be automatically, such as by software, or manually identified and saved 308. The customer specific data and/or customer protocol data identified and saved may relate to the type of hardware, the hardware configuration, the software configuration, measurement protocols generated by the customer, customer software or hardware settings, customer machine type and/or specifications, and network information. Additional, fewer, or alternate types of data also may be identified and saved accessing the customer machine.

The customer specific data and/or customer protocol data may be transferred to the virtual machine 310. The customer specific data and/or customer protocol data may be transmitted to the virtual machine via remote connection, such as the Internet or other network, given enough available bandwidth. The customer specific data and/or customer protocol data also may be transferred to the virtual machine via portable storage medium, such as digital versatile disc, compact disc, or other electronic storage units. Alternate methods of transferring the customer specific data and/or customer protocol data to the virtual machine may be used.

A software technician or engineer may integrate the customer specific data with the upgraded version of the software application by re-inputting the customer specific data 312. Additionally, the software engineer may modify the upgraded version of the software application to become compatible with the customer protocols 314.

Alternatively, the virtual machine may automatically integrate the customer specific data with the upgraded version of the software application. The virtual machine may customize the upgraded version of the software application by fully or partially automatically re-inputting the customer specific data 312. Additionally, the data processing system may fully or partially automatically modify the upgraded version of the software application to become compatible with the customer protocols 314.

A customer software license may be reissued 316 by the virtual machine. The customer software license may be automatically generated by the virtual machine.

An executable version of the upgraded version of the software application as modified may be generated 318 by the virtual machine that accounts for the customer specific data and/or customer protocols. Hence, the executable version may be a tailored and customized version of the upgraded software application.

Additionally, the executable version of the modified upgraded version may be tested on the virtual machine. The virtual machine may be operating in a virtual mode that mimics the operation of the customer machine during the testing. Any problems with the modified upgraded version may be manually identified and troubleshot using the virtual machine.

Alternatively, the virtual machine may include rule sets and tables of most likely errors that are automatically searched for within the code of the modified upgraded version of the software application. As an example, rules may identify and be used to automatically search for errors associated with user specifications, protocols, settings, customizations, configurations, and machine types that are incompatible with the current upgraded version or modified upgraded version of the software. Other rules may be used.

If any of the pre-determined errors are identified, the virtual machine may replace corresponding code in the modified upgraded version to attempt to remedy the problem. If the virtual machine is incapable of automatically identifying and correcting the problem, a warning may be generated to the software technician carrying out the upgrade process that identifies the problem for subsequent manual troubleshooting.

After which, the executable modified upgraded version of the software application may be transferred to the customer machine. The modified upgraded version of the software application may be transmitted to the customer machine via remote connection, such as the Internet or other network, available bandwidth permitting. The software application also may be transferred to the customer machine via a portable storage medium, such as digital versatile disc, compact disc, or other electronic storage unit. Alternate methods of transferring the modified upgraded version of the software application to the customer machine may be used.

The modified upgraded version of the software application may be installed on the customer machine 320. An optional functional test of the customer's system 322 may then be performed. With some upgraded software applications, additional customer specific data may be identified 324. For example, the revised version of the software application may include additional features and functions that may be modified or customized by the user. The technique for upgrading a software application via a virtual machine may include additional, fewer, or alternative steps.

Figure 4:
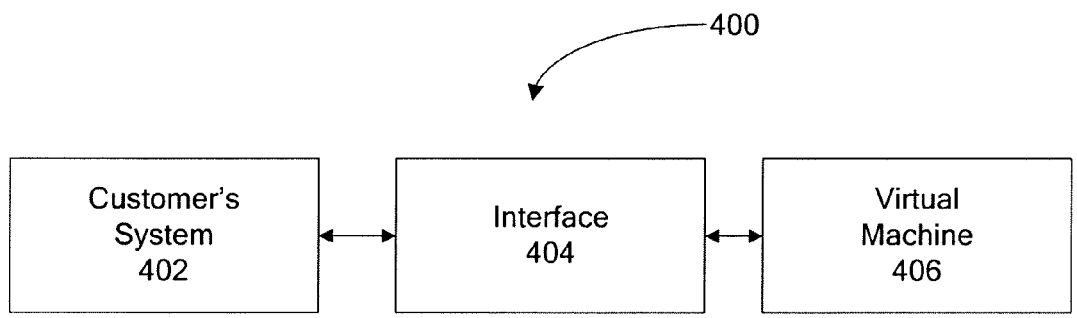
FIG. 4 is an exemplary interface for upgrading a software application offline via a virtual machine.

FIG. 4 is exemplary interface for upgrading a software application offline via virtual machine 400. As shown, the virtual machine interface 304 may be configured to communicate with both the customer's system 302 and the virtual machine 306, such as to facilitate transferring data between the two. The virtual machine interface 304 may need to be altered for each different customer machine 302. For instance, customer machines may have different operating systems, such as MS-DOS or Linux, or different user interfaces, settings, and configurations. The virtual machine interface 304 may support direct or remote interconnectivity with the customer machine 306. Interfaces with additional, less, or alternate functionality may be used.

III. Exemplary Virtual Machine

Figure 5:
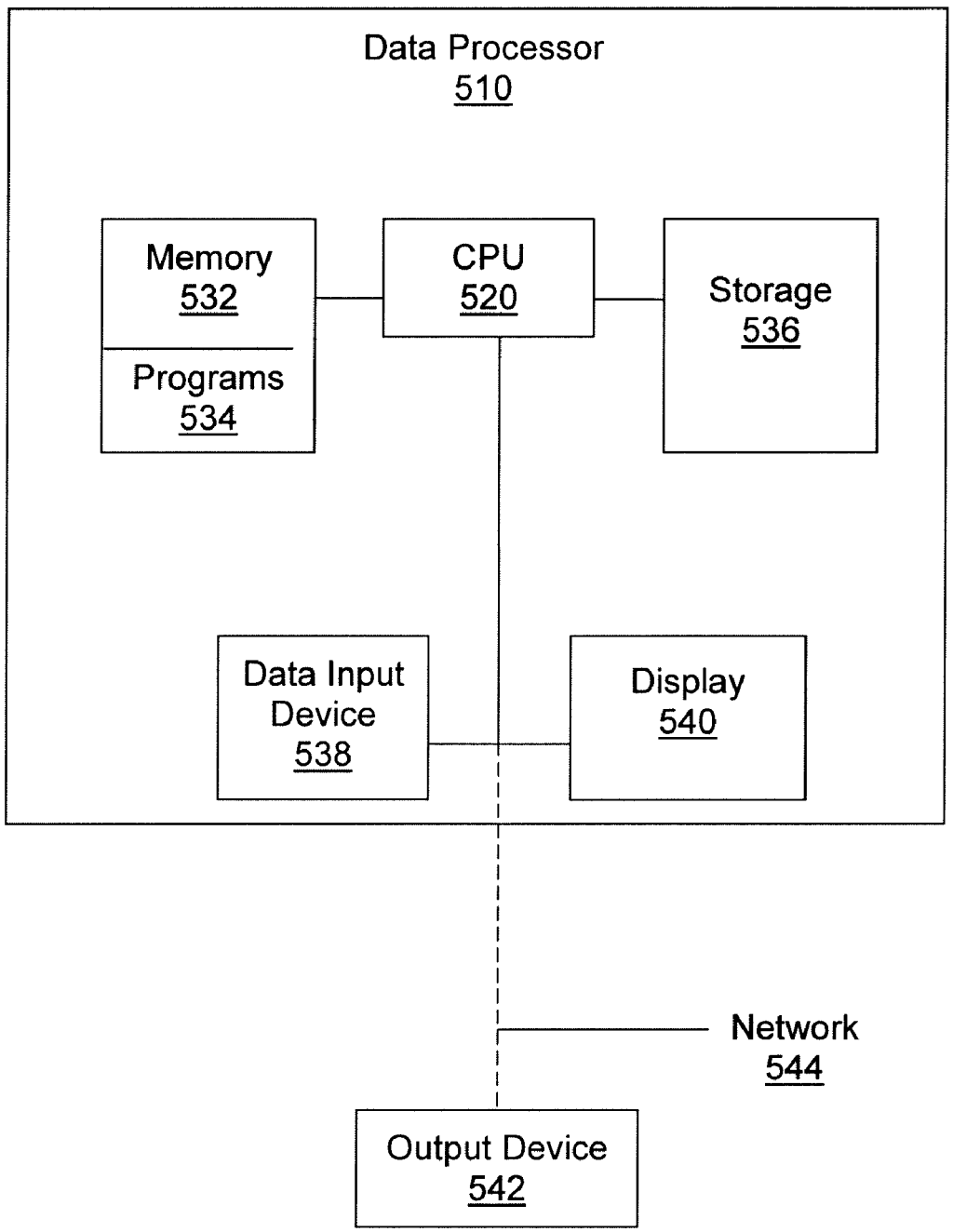
FIG. 5 illustrates an exemplary data processor configured or adapted to provide the functionality of a virtual machine for upgrading a software application offline.

FIG. 5 illustrates an exemplary data processor or virtual machine 10 configured or adapted to provide the functionality for upgrading software applications offline. The virtual machine 510 may include a central processing unit (CPU) 520, a memory 532, a storage device 536, a data input device 538, and a display 540. The virtual machine 510 also may have an external output device 542, which may be a display, a monitor, a printer or a communications port. The virtual machine 510 may be a personal computer, work station, or other computing system. The virtual machine 510 may be interconnected to a network 544, such as an intranet, the Internet, or an intranet connected to the Internet. The virtual machine 510 may be interconnected to a customer system or location via the network 544. The virtual machine 510 is provided for descriptive purposes and is not intended to limit the scope of the present system. The processor may have additional, fewer, or alternate components.

A program 534 may reside on the memory 532 and include one or more sequences of executable code or coded instructions that are executed by the CPU 520. The program 534 may be loaded into the memory 532 from the storage device 536. The CPU 520 may execute one or more sequences of instructions of the program 534 to process data. Data may be input to the virtual machine 510 with the data input device 538 and/or received from the network 544 or customer system. The program 534 may interface the data input device 538 and/or the network 544 or customer system for the input of data. Data processed by the virtual machine 510 may be provided as an output to the display 540, the external output device 542, the network 544, the customer system, and/or stored in a database. The program 534 and other data may be stored on or read from machine-readable medium, including secondary storage devices such as hard disks, floppy disks, CD-ROMS, and DVDs; electromagnetic signals; or other forms of machine readable medium, either currently known or later developed.

In one embodiment, the virtual machine 510 may provide functionality that simulates one or more operations of the actual customer machine on which a previous version of a software application operates. Alternate virtual machines may be used, including those discussed elsewhere herein.

An upgraded or revised version of the software application may be received by the virtual machine 510 from the data input device 538, the network 544, or another input device. After which, the upgraded version of the software application may be stored in the memory 532, the storage device 536, or other storage unit.

Customer specific data and/or customer protocol data related to the previous version of a software application may be received from a customer machine by the virtual machine 510 via the data input device 538, the network 544, the customer system, or another input device. The virtual machine 510 may modify the upgraded version of the software application using the customer specific data and/or the customer protocol data.

The virtual machine 510 may integrate the customer specific data with the upgraded version of the software application to modify the upgraded version. The integration of the customer specific data with the upgraded version by the virtual machine 510 may be fully or partially automated. The modified upgraded version may substantially replicate or restore the user interface and other user specific settings of the previous version of the software application on the display 540, output device 542, a customer machine located at the customer site, or other display device.

The virtual machine 510 may convert the customer protocol data to become compatible with the upgraded version of the software application. The virtual machine 510 may then generate an executable version of the upgraded version of the software application that takes into account the customer specific data and/or the customer protocols. The conversion of the customer protocol data to become compatible with the upgraded version of the software application, as well as the generation of an executable version, by the virtual machine 510 may be fully or partially automated.

The virtual machine 510 may generate a customer software license tailored toward the modified upgraded version of the software application. The software license may be transferred to the customer via the network 544, the output device 542, or other manner.

The executable version of the modified upgraded version of the software application may then be transferred to the customer location via the network 544, the output device 542, or other manner. The executable version transferred to the customer location may then be installed and tested on the customer machine.

The virtual machine 510 may modify the upgraded version of the software application using the customer related data. For instance, the virtual machine 510 may correlate the customer related data to settings and other modifications with the upgraded version that need to be made to make the upgraded version compatible with the actual customer machine. The virtual machine 510 may implement a set of rules or data structures to correlate the modifications. The virtual machine 510 may test the modified upgraded version, such as by operating in a virtual mode that simulates the actual customer machine and/or by checking that appropriate modifications have been implemented.

In one embodiment, the virtual machine 510 may only receive either customer specific data or customer protocol data from the customer machine via the data input device 538, the network 544, the customer system, or other input device. The virtual machine 510 may modify the upgraded version of the software application using only the customer specific data or the protocol data. The virtual machine 510 may transfer the modified upgrade to the customer machine via the network 544, the output device 542, or other method. Once on the customer machine, the modified upgraded version of the software application may be run with only minimal or no further modifications.

In another embodiment, the program 534 may include instructions that direct the operation of a virtual machine that mimics a customer machine in a virtual machine mode, receiving customer related data from the customer machine related to a previous version of a software application installed on the customer machine, and modifying an upgraded version of the software application based upon the customer related data. The instructions also may direct testing the modified upgraded version of the software application via the virtual machine operating in the virtual machine mode to verify that the modified upgraded version is executable on the customer machine, and transferring the modified upgraded version of the software application to the customer machine for use.

IV. Exemplary Medical Software Applications

In one embodiment, the software applications are directed toward the medical field. The customer locations may be hospitals, clinics, or other medical facilities. The customer personnel may include doctors, nurses, and other medical personnel. The software applications may assist the medical personnel with the diagnosis of medical conditions and the treatment of patients.

The software applications used on the actual customer machines may relate to processing images illustrating an enhanced region of interest within a patient. For example, various types of contrast medium may be administered to a medical patient. The contrast mediums enhance the scans acquired by scanning a patient or images of the patient, the scans and images may be recorded by an external recording device as enhancement data. The contrast medium typically travels through a portion of the body, such as in the blood stream, and reaches an area that medical personnel are interested in analyzing. While the contrast medium is traveling through or collected within a region of interest, a series of scans or images of the region of interest of the patient may be recorded for processing and display by the software applications. The enhanced region of interest may show the brain, the abdomen, the heart, the liver, a lung, a breast, the head, a limb or any other body area.

The software applications may support one or more specific type of imaging processes that are used to produce images of the patient. In general, the software applications may support imaging processes such as radiography, angioplasty, computerized tomography, ultrasound and magnetic resonance imaging (MRI). Additional types of imaging processes that may be supported by the software include perfusion and diffusion weighted MRI, cardiac computed tomography, computerized axial tomographic scan, electron-beam computed tomography, radionuclide imaging, radionuclide angiography, single photon emission computed tomography (SPECT), cardiac positron emission tomography (PET), digital cardiac angiography (DSA), and digital subtraction angiography (DSA). Alternate imaging processes may be supported by the software applications.

Each software application may have customer protocols dependent upon the type of imaging process(es) or imaging processing device that the software application supports. The customer protocols may comprise all of the settings for the operating machines and medical imaging modules and subroutines associated with the software application in order to generate medical image data. The settings may be manufacturer, supplier, or distributor specific or may be customized by the customer. For example, the customer protocols may account for the type of machine used by the customer and/or comprise settings for magnetic resonance imaging devices, computer tomography devices, and other imaging processes devices, including, but not limited to, devices pertaining to the imaging processes mentioned directly above.

The customer protocols also may account for the respective image type. For instance, the customer protocols may account for images generated by angiographic, orthopedic, or other imaging processes, including, but not limited to, the imaging processes mentioned directly above. Additionally, the customer protocols may account for the location of the region of interest displayed in the images, such as the cranium, the brain, the abdomen, the heart, the liver, a lung, a breast, the head, a limb, the torso, or any other body area.

Additionally, as noted above, the customer specific data may pertain to a customized user interface of the previous version of the software application. For instance, each medical software application may use customer specific data related to displaying customized windows or text boxes that present messages to be displayed and accept directions from a user, such as what information is to be analyzed. The customer specific data also may pertain to displaying one or more customized floating windows to present analyzed data and generate text messages with recommendations and diagnosis. The customer specific data also may relate to customized software tool tips that may enhance the effectiveness and the efficiency of the users utilizing the software. The tool tips may be accessible from a menu or pop-up window that the user accesses via a mouse, keyboard, touchpad, or other input device. The customer specific data may pertain to additional, fewer, or alternate user specific settings and customizations.

The virtual machine may modify an upgraded version of a software application for a number of customer machines using the same revised version of the software application as a starting point. The modification of the upgraded version of the software application for each customer machine may be different based upon the customer specific data and customer protocols utilized by each customer machine. Therefore, each modified upgraded version of the software application may be different. The difference between each modified upgraded version of the software application may be dependent upon the individual customization required by each customer.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

It is therefore intended that the foregoing detailed description be regarded as illustrative rather than limiting, and that it be understood that it is the following claims, including all equivalents, that are intended to define the spirit and scope of this invention.

What is claimed is:

1. A method for upgrading software offline using a virtual machine, the method comprising:
   creating a virtual machine that mimics an operation of an actual customer machine that is part of a medical imaging system that acquires internal anatomical images;
   loading an upgraded version of a software application onto the virtual machine;
   loading customer specific data related to a previous version of the software application onto the virtual machine, the previous version of the software application being installed and used on the actual customer machine;
   modifying the upgraded version of the software application on the virtual machine using the customer specific data such that the upgraded version of the software application as modified is compatible with the actual customer machine without further modification;
   testing the modified upgraded version of the software application on the virtual machine to ensure that the modified upgraded version has been properly modified to include the customer specific data related to the previous version of the software application;
   automatically identifying a problem with the modified upgraded version of the software application running on the virtual machine;
   automatically altering the modified upgraded version to correct the problem associated with running the modified upgraded version of the software application on the customer machine based upon a pre-determined rule set; and
   transferring the upgraded version of the software application as modified from the virtual machine to the actual customer machine for use on the actual customer machine,
   wherein the pre-determined rule set correlates the customer related data with pre-determined modifications to the upgraded version of the software application that must be accomplished to ensure compatibility with the customer machine, and
   wherein the pre-determined rule set comprises a list of common errors associated with user specifications, protocols, settings, customizations, configurations, or combinations thereof, that are incompatible with the modified upgraded version of the software application.

2. The method of claim 1, the method comprising:
   identifying problems with the operation of the upgraded version of the software application as modified while testing the upgraded version of the software application as modified on the virtual machine in an operating mode that mimics the operation of the actual customer machine; and
   revising the upgraded version of the software application as modified to correct the problems identified during the testing of the upgraded version of the software application as modified on the virtual machine.

3. The method of claim 1, wherein the customer specific data is used by the virtual machine to mimic a customized user interface of the previous version of the software application as used on the actual customer machine when running the upgraded version of the software application as modified.

4. The method of claim 1, wherein the actual customer machine is a medical computer system, and the software application assists medical treatment.

5. The method of claim 4, wherein the software application displays medical images on a screen associated with the actual customer machine, and customer protocols account for medical imaging modules of the software application.

6. The method of claim 1, the method comprising using a software program to automatically identify the customer specific data related to a previous version of the software application as implemented on the customer machine by which to modify the upgraded version.

7. The method of claim 1, wherein (1) data associated with the previous version of the software application is transferred from the actual customer machine to the virtual machine, and (2) the upgraded version of the software application as modified is transferred from the virtual machine to the actual customer machine via a remote network interconnection.

8. The method of claim 1, wherein transferring comprises transferring the upgraded version from the virtual machine to the actual customer machine while the medical imaging system is simultaneously acquiring internal anatomical images.

9. The method of claim 1, wherein testing comprises verifying that variables or settings within the modified upgraded version correspond with customer settings, modifications, customizations, or combinations thereof, identified by the customer specific data related to the previous version of the software application.

10. The method of claim 1, wherein automatically identifying comprises automatically searching a code of the modified upgraded version for one or more errors from the list of common errors, and
    wherein automatically altering comprises automatically replacing, when the one or more errors from the list of common errors are identified, a portion of the code that corresponds to the one or more errors.

11. A method for upgrading software offline via a virtual machine, the method comprising:
    loading an upgraded version of a software application onto a virtual machine that is configured to mimic an operation of a customer machine that is part of a medical imaging system that acquires internal anatomical images;
    transferring customer protocol data identifying customer protocols related to a previous version of the software application installed and used on the customer machine from the customer machine onto the virtual machine;
    modifying the upgraded version of the software application to become compatible with the customer machine using the virtual machine and the customer protocol data;
    testing the modified upgraded version of the software application on the virtual machine to ensure that the modified upgraded version has been properly modified to include the customer protocol data originally related to the previous version of the software application;

automatically identifying a problem with the modified upgraded version of the software application running on the virtual machine;

automatically altering the modified upgraded version to correct the problem associated with running the modified upgraded version of the software application on the customer machine based upon a pre-determined rule set; and transferring the modified upgraded version of the software application from the virtual machine to the customer machine such that the modified upgraded version of the software application is runnable on the customer machine, wherein the pre-determined rule set correlates the customer related data with pre-determined modifications to the upgraded version of the software application that must be accomplished to ensure compatibility with the customer machine, and wherein the pre-determined rule set comprises a list of common errors associated with user specifications, protocols, settings, customizations, configurations, or combinations thereof, that are incompatible with the modified upgraded version of the software application.

12. The method of claim 11, the method comprising using a software program to automatically identify the customer protocol data related to a previous version of the software application as implemented on the customer machine by which to modify the upgraded version.

13. The method of claim 12, wherein (1) the customer protocol data associated with the previous version of the software application is transferred from the customer machine to the virtual machine, and (2) the modified upgraded version of the software application is transferred from the virtual machine to the customer machine via a remote network interconnection.

14. The method of claim 11, wherein the software application displays medical images on a screen associated with the customer machine, and the customer protocol data accounts for medical imaging modules associated with the software application and the type of customer machine on which the software application operates.

15. The method of claim 11, wherein the customer protocol data is used by the modified upgraded version of the software application to substantially replicate a customized user interface of the previous version of the software application as used on the customer machine.

16. A virtual machine for upgrading software offline, the virtual machine comprising:

a memory unit storing an upgraded version of a software application; and a processing unit configured to receive, from a customer machine that is part of a medical imaging system that acquires internal anatomical images, customer specific data related to the operation of a previous version of the software application on a customer machine, wherein the virtual machine is configured to automatically modify the upgraded version of the software application stored in the memory unit based upon the customer specific data received by the processing unit and creates an executable modified upgraded version of the software application that is runnable by the customer machine without further modification, wherein the virtual machine is configured to test the automatically modified upgraded version of the software application to verify that the modified upgraded version has been properly modified to include the customer specific data related to the operation of the previous version of the software application originally received from the customer machine, wherein the virtual machine is configured to automatically identify a problem with the modified upgraded version of the software application running on the virtual machine, wherein the virtual machine is configured to automatically alter the modified upgraded version to correct the problem associated with running the modified upgraded version of the software application on the customer machine based upon a pre-determined rule set, wherein the pre-determined rule set correlates the customer related data with pre-determined modifications to the modified upgraded version of the software application that must be accomplished to ensure compatibility with the customer machine, wherein the pre-determined rule set comprises a list of common errors associated with user specifications, protocols, settings, customizations, configurations, or combinations thereof, that are incompatible with the modified upgraded version of the software application, and wherein the virtual machine is configured to transfer the modified upgraded version of the software application to the customer machine such that the modified upgraded version of the software application is runnable on the customer machine.

17. The system of claim 16, wherein the virtual machine modifies the upgraded version of the software application such that a user interface of the modified upgraded version of the software application is substantially identical to a customized user interface of the previous version of the software application as used on the customer machine.

18. A non-transitory computer-readable medium having instructions executable on a computer stored thereon, the instructions comprising:

directing a virtual machine that mimics a customer machine in a virtual machine mode, the customer machine being part of a medical imaging system that acquires internal anatomical images;

receiving customer related data from the customer machine related to a customer used, previous version of a software application installed on the customer machine;

modifying an upgraded version of the software application based upon the customer related data;

testing the modified upgraded version of the software application via the virtual machine operating in the virtual machine mode to verify that the modified upgraded version is executable on the customer machine;

testing the modified upgraded version of the software application on the virtual machine to ensure that the modified upgraded version has been properly modified to include the customer related data originally related to the previous version of the software application;

automatically identifying a problem with the modified upgraded version of the software application running on the virtual machine in the virtual machine mode;

automatically altering the modified upgraded version to correct the problem associated with running the modified upgraded version of the software application on the customer machine based upon a pre-determined rule set; and transferring the modified upgraded version of the software application to the customer machine for use, wherein the pre-determined rule set correlates the customer related data with pre-determined modifications to the upgraded version of the software application that must be accomplished to ensure compatibility with the customer machine, and wherein the pre-determined rule set comprises a list of common errors associated with user specifications, protocols, settings, customizations, configurations, or combinations thereof, that are incompatible with the modified upgraded version of the software application.

19. The non-transitory computer-readable medium of claim 18, wherein the software application directs the acquisition of internal medical images using computed tomography or magnetic resonance techniques.

20. The non-transitory computer-readable medium of claim 18, wherein automatically identifying comprises automatically searching a code of the modified upgraded version for one or more errors from the list of common errors, and wherein automatically altering comprises automatically replacing, when the one or more errors from the list of common errors are identified, a portion of the code that corresponds to the one or more errors.

* * * * *